(12) United States Patent
Wang et al.

(10) Patent No.: US 9,714,250 B2
(45) Date of Patent: Jul. 25, 2017

(54) CRYSTALLINE FORMS OF TEMOZOLOMIDE AND THE METHOD FOR PREPARING SAME

(71) Applicant: Jiangsu Tasly Diyi Pharmaceutical Co., Ltd., Huai'an (CN)

(72) Inventors: Guocheng Wang, Tianjin (CN); Wenzheng Liu, Tianjin (CN); Yuzhe Gao, Tianjin (CN); Hailong Yang, Tianjin (CN); Qingwei Hou, Tianjin (CN); Yu Zhang, Tianjin (CN)

(73) Assignee: Jiangsu Tasly Diyi Pharmaceutical Co., Ltd., Huai'an (CN)

( * ) Notice: Subject to any disclaimer, the term of this patent is extended or adjusted under 35 U.S.C. 154(b) by 0 days.

(21) Appl. No.: 15/033,242

(22) PCT Filed: Oct. 28, 2014

(86) PCT No.: PCT/CN2014/089713
§ 371 (c)(1),
(2) Date: Apr. 29, 2016

(87) PCT Pub. No.: WO2015/062481
PCT Pub. Date: May 7, 2015

(65) Prior Publication Data
US 2016/0289234 A1    Oct. 6, 2016

(30) Foreign Application Priority Data
Oct. 29, 2013    (CN) .......................... 2013 1 0521569

(51) Int. Cl.
C07D 487/04    (2006.01)
A61K 31/4188    (2006.01)

(52) U.S. Cl.
CPC ........ *C07D 487/04* (2013.01); *C07B 2200/13* (2013.01)

(58) Field of Classification Search
CPC ..................................................... C07D 487/04
USPC .......................................... 544/179; 514/183
See application file for complete search history.

(56) References Cited

U.S. PATENT DOCUMENTS 7,612,202 B2    11/2009    Etlin

FOREIGN PATENT DOCUMENTS

| CN | 1706843 C | 12/2005 |
| CN | 1730482 C | 2/2006 |
| CN | 102659789 A | 9/2012 |
| EP | 2151442 A2 | 2/2010 |

OTHER PUBLICATIONS

IN 272907, Patent granted May 6, 2016, filed Jul. 19, 2013, effective priority Jan. 18, 2016; Specification from Indian Patent Office provided.*
Narode, IN272907, SciFinder Abstract Sep. 17, 2016.*

* cited by examiner

*Primary Examiner* — Venkataraman Balasubramanian
(74) *Attorney, Agent, or Firm* — IP Attorneys Group, LLC

(57) ABSTRACT

Provided in the present invention are a new method for preparing the crystalline forms of Temozolomide and three types of crystalline form of Temozolomide by the method. Said method comprises the following steps: a Temozolomide is dissolved into dimethyl sulphoxide, a second organic solvent is added for recrystallization to prepare the crystalline forms of Temozolomide, wherein the second organic solvent is an alcohol, a ketone, a halohydrocarbon or an ester.

9 Claims, 11 Drawing Sheets

CRYSTALLINE FORMS OF TEMOZOLOMIDE AND THE METHOD FOR PREPARING SAME

CROSS-REFERENCE TO RELATED APPLICATION

This application is a national phase entry of International Application No. PCT/CN2014/089713, filed Oct. 28, 2014 and titled "The Crystalline Forms of Temozolomide and the Method for Preparing Same," which claims priority to and the benefit of Chinese Patent Application No.: 201310521569.8, filed Oct. 29, 2013 and titled "The Crystalline Forms of Temozolomide and the Method for Preparing Same." The contents of the above-identified Applications are relied upon and incorporated herein by reference in their entirety.

FIELD OF THE INVENTION

The present invention belongs to the pharmaceutical field and relates to crystalline forms of pharmaceutical compound. More specifically, the present invention relates to crystalline forms of an anti-tumor drug Temozolomide and the method for preparing thereof.

BACKGROUND OF THE INVENTION

Temozolomide (TMZ) is an alkylating anti-tumor drug containing an imidazotetrazine ring with an anti-tumor activity. Its chemical structure is presented as follows:

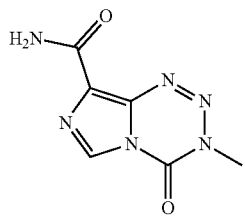

Temozolomide belongs to a pro-drug with no activity. It is usually converted to the active compound MITC (5-(3-methyltriazen-1-yl)-imidazole-4-carboxamide) under a physiological pH level via a non-enzymatic pathway, and MITC is further hydrolyzed to an active metabolite, showing its anti-tumor activity. In theory, the anti-tumor activity of MTIC is mainly produced by major DNA alkylation (methylation) with the $6^{th}$ oxygen atom of guanine. Also, it can have secondary additional alkylation with the $7^{th}$ nitrogen atom of guanine. Therefore, the subsequent cytotoxicity is considered to have the relationship with these abnormally-repaired methyl compounds.

Temozolomide compounds have been already synthesized. In recent years, however, it is continuously found that its new crystalline forms have excellent medicinal value. For example, U.S. Pat. No. 5,260,291 disclosed Temozolomide polymorphs prepared by using the following three different solvent systems: acetone and water (3:1), acetone and water (1:3), and water. *Chinese Journal of Pharmaceuticals* reproduced the method of U.S. Pat. No. 5,260,291, and reported the relevant data; US 20050187206 disclosed the methods for preparing various crystalline forms of Temozolomide by using a variety of solvents, such as pyridine, ethanol, acetone etc.; WO2008111092 disclosed Temozolomide monohydrate, prepared by the solvent of acetone and water (3:1); Chinese patent CN201110201186.3 disclosed a type of crystalline form of Temozolomide prepared by using a mixed solvent of acetone, acetonitrile and water.

The afore-mentioned methods have a problem caused by the solubility of TMZ, i.e. a large amount of solvent, which is up to a few times or even hundreds of times of Temozolomide, are required for dissolution, for example, in US20050187206, the amount of ethanol reached 270 times the amount of Temozolomide (v/w), and the amount of acetone used even reached more than 300 times the amount of Temozolomide (v/w). Alternatively, although the volume of the solvent is more than 10 times the amount of Temozolomide, the yield is low, thus it is unsuitable for industrial production. In addition, the crystalline forms prepared by the above-mentioned methods are unstable, e.g. in US20050187206, crystalline Form I of Temozolomide was transformed into crystalline Form II under a condition of being heated to approximately 30° C.

Therefore, it is necessary to find a stable crystalline form of Temozolomide for medicine application, specifically as an active pharmaceutical ingredient (API) in a solid pharmaceutical. In addition, the solvents used in the recrystallization methods of Temozolomide in the prior art were short of specificity, so that a small amount of impurities was contained in the obtained crystalline forms of Temozolomide. As a result, the application was affected.

CONTENT OF THE INVENTION

In order to solve the above problems, the present invention provides a novel method for preparing crystalline forms of Temozolomide and the crystalline forms prepared by the method.

According to the first aspect, the present invention provides a novel method for preparing crystalline forms of Temozolomide, characterized in that, the method comprises the following steps: dissolving Temozolomide in dimethylsulfoxide (DMSO), into which a second organic solvent is added for recrystallization, whereby the crystalline forms of Temozolomide are prepared. Wherein, the second organic solvent is an alcohol, a ketone, a halohydrocarbon or an ester. Preferably, the second organic solvent is ethanol, methanol, isopropanol, acetone, dichloromethane, ethyl acetate or glycol.

The method of the present invention for preparing crystalline forms of Temozolomide comprises the following steps: Temozolomide is prepared, into which DMSO with 7-20 times the amount of the Temozolomide (v/w) is added, the mixture of Temozolomide and DMSO is stirred and heated to make the Temozolomide dissolved, then a second organic solvent with 5-30 times the amount of the Temozolomide (v/w) is added, stirred, cooled down, crystallized by stirring, filtered to give the crystalline forms, and the resultant crystalline forms are washed by using the second organic solvent with 2-10 times the amount of the Temozolomide (v/w), and dried in vacuum to give the crystalline forms of Temozolomide.

More specifically, the method of the present invention for preparing crystalline forms of Temozolomide comprises the following steps: Temozolomide is prepared, into which DMSO with 7-15 times the amount of the Temozolomide (v/w) is added, the mixture of Temozolomide and DMSO is stirred and heated to 60-140° C. to make the Temozolomide dissolved, then a second organic solvent with 7-20 times the amount of the Temozolomide (v/w) is added, stirred for 5-15min, cooled down to 10-15° C., crystallized for 4 hours by stirring, filtered to give the crystalline forms, and the resultant crystalline forms are washed by using the second organic solvent with 2-5 times the amount of the Temozolomide (v/w), and dried in vacuum to give the crystalline forms of Temozolomide.

It should be noted that, in the method of the present invention for preparing crystalline forms of Temozolomide, no special requirements are needed on the stirring equipment and stirring speed during the formation of the three crystalline forms. Conventional stirring equipment and stirring speed can be used for preparing the crystalline forms.

The crystalline forms prepared by the method of the present invention are identified and confirmed to be three crystalline forms: Form A, Form B and Form C.

Wherein, when the second organic solvent is selected from ethanol or methanol, the crystalline forms are identified to be the same form and designated as Form A; when the second organic solvent is selected from isopropanol, acetone, dichloromethane or ethyl acetate, the crystalline forms are identified to be the same form and designated as Form B; when the second organic solvent is glycol, the crystalline form is designated as Form C.

MODE OF CARRYING OUT THE INVENTION

The following specific parameters are used to describe various crystalline forms of the present invention. In the present invention, X-ray Powder Diffraction (XRPD), Thermo gravimetry-Differential Thermal Analysis (TG-DTA) and Infra-Red (IR) measurement conditions are presented as follows:

XRPD:

Apparatus: Savitzkey-Golay type X-ray Diffractometer, test conditions: 40 kv 100 mA;

Slit: DS/SS=1°, RS=0.3 mm; Step: 0.02; target type: copper target, 1.5405 Å; Range: 3-50°; scan rate: 8°/min.

TG-DTA:

Apparatus: Rigaku PTC-10A TG-DTA analyzer; range: 7 mg;

Temperature range: room temperature-300° C.; heating rate: 10° C./min; DTA range: ±25 μv.

IR:

Apparatus: SHIMADZU FTIR-8400S FT/IR type infrared spectroscopy, wave number was corrected by infrared absorption peak of polystyrene film; Method: KBr tablet method, recording spectrum in a range of 4000-400 $cm^{-1}$.

Figure 1:
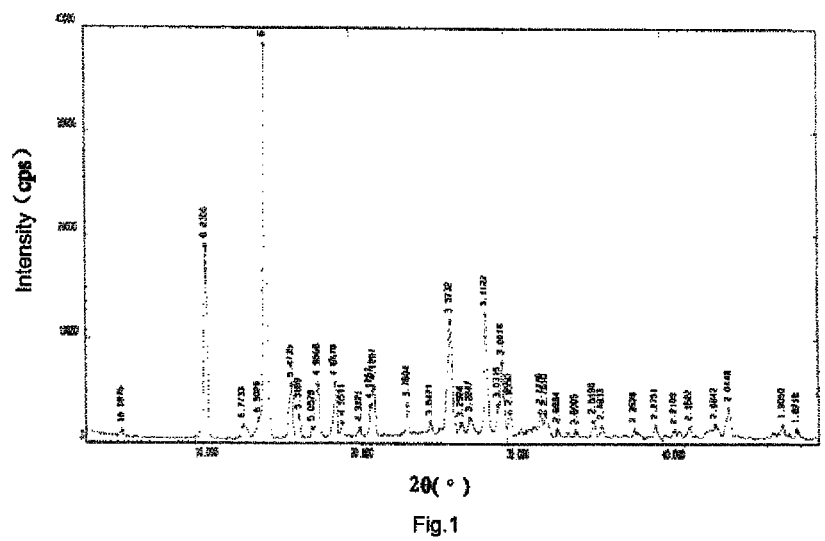
FIG. 1 is the X-ray diffraction pattern of Form A0 prepared by using ethanol as the second organic solvent.

In one embodiment of the present invention, when the second organic solvent is ethanol, the obtained crystalline form of Temozolomide is named as Form A0 type, characterized by powder X-ray diffraction spectrum comprising characteristic diffraction peaks expressed in terms of 2θ at 10.74±0.2, 14.54±0.2, 26.40±0.2, 28.66±0.2 and 29.74±0.2. Specific X-ray diffraction data are shown in Table 1 and the X-ray diffraction pattern is shown in FIG. 1.

TABLE 1

Characteristic peak parameters of X-ray diffraction pattern of Form A0

| Nos. | 2θ | d value | Relative intensity $I/I_0$ |
|---|---|---|---|
| 1 | 5.320 | 16.5976 | 3 |
| 2 | 10.740 | 8.2306 | 49 |
| 3 | 13.060 | 6.7733 | 4 |
| 4 | 14.040 | 6.3026 | 6 |
| 5 | 14.540 | 6.0870 | 100 |
| 6 | 16.180 | 5.4735 | 15 |
| 7 | 16.660 | 5.3169 | 7 |
| 8 | 17.520 | 5.0578 | 4 |
| 9 | 17.880 | 4.9568 | 15 |
| 10 | 19.000 | 4.6670 | 15 |
| 11 | 19.480 | 4.5531 | 5 |
| 12 | 20.580 | 4.3121 | 4 |
| 13 | 21.260 | 4.1757 | 9 |
| 14 | 21.500 | 4.1297 | 14 |
| 15 | 23.640 | 3.7604 | 10 |
| 16 | 25.120 | 3.5421 | 5 |
| 17 | 26.400 | 3.3732 | 31 |
| 18 | 27.060 | 3.2924 | 5 |
| 19 | 27.640 | 3.2247 | 6 |
| 20 | 28.660 | 3.1122 | 33 |
| 21 | 29.440 | 3.0315 | 10 |
| 22 | 29.740 | 3.0016 | 20 |
| 23 | 30.220 | 2.9550 | 8 |
| 24 | 32.200 | 2.7776 | 8 |
| 25 | 32.520 | 2.7510 | 8 |
| 26 | 33.300 | 2.6884 | 4 |
| 27 | 34.460 | 2.6005 | 3 |
| 28 | 35.600 | 2.5198 | 6 |

TABLE 1-continued

Characteristic peak parameters of X-ray diffraction pattern of Form A0

| Nos. | 2θ | d value | Relative intensity I/I₀ |
|---|---|---|---|
| 29 | 36.140 | 2.4833 | 4 |
| 30 | 38.220 | 2.3528 | 4 |
| 31 | 39.580 | 2.2751 | 5 |
| 32 | 40.780 | 2.2109 | 4 |
| 33 | 41.740 | 2.1622 | 4 |
| 34 | 43.380 | 2.0842 | 5 |
| 35 | 44.260 | 2.0448 | 9 |
| 36 | 47.700 | 1.9050 | 5 |
| 37 | 48.600 | 1.8718 | 4 |

Figure 8:
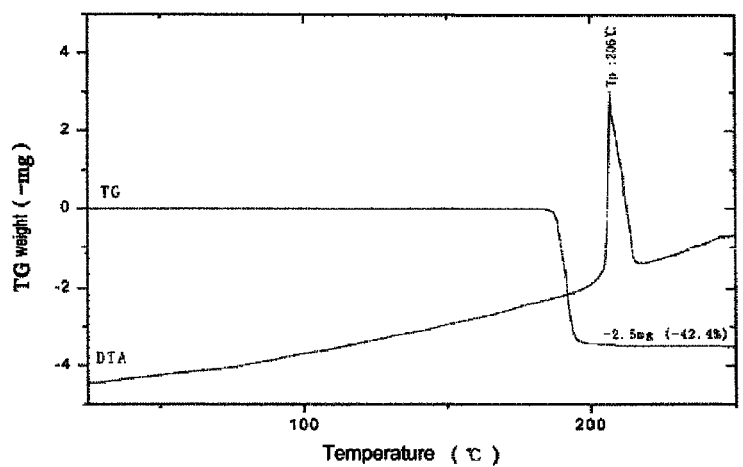
FIG. 8 is the TG-DTA chart of Form A0 prepared by using ethanol as the second organic solvent.

As shown in TG-DTA spectrum, Form A0 has an exothermic peak at 206° C. (FIG. 8).

Figure 15:
FIG. 15 is the infrared absorption spectrum of Form A0 prepared by using ethanol as the second organic solvent.

As shown in the infrared absorption spectrum data, Form A0 has characteristic absorption peaks at 3423.41, 3388.70, 3114.82, 1755.10, 1728.10, 1681.81, 1452.30, 1265.22 and 948.91 cm$^{-1}$ (FIG. 15).

Figure 2:
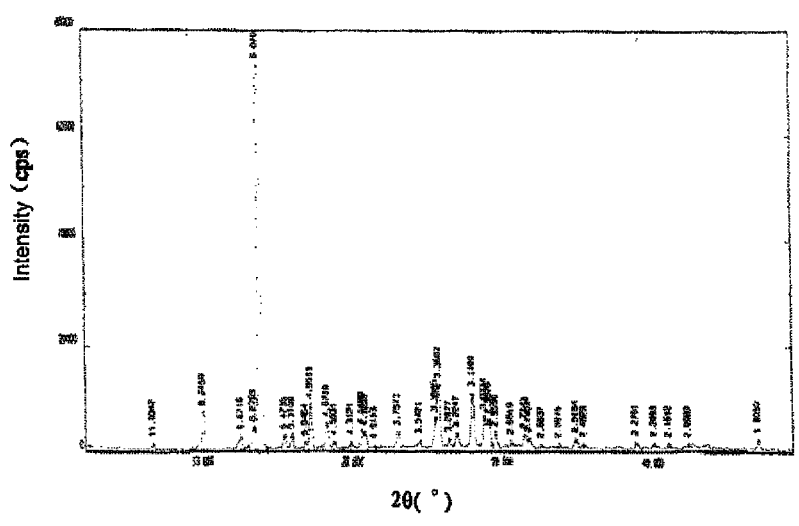
FIG. 2 is the X-ray diffraction pattern of Form A1 prepared by using methanol as the second organic solvent.

In another embodiment of the present invention, when the second organic solvent is methanol, the resultant crystalline form of Temozolomide is named as Form A1, characterized by powder X-ray diffraction spectrum comprising characteristic diffraction peaks expressed in terms of 2θ at 10.72±0.2, 14.58±0.2, 17.90±0.2, 26.44±0.2 and 28.68±0.2. Specific X-ray diffraction data are shown in Table 2, and the X-ray diffraction pattern is shown in FIG. 2.

TABLE 2

Characteristic peak parameters of X-ray diffraction pattern of Form A1

| Nos. | 2θ | d value | Relative intensity I/I₀ |
|---|---|---|---|
| 1 | 7.420 | 11.9042 | 2 |
| 2 | 10.720 | 8.2459 | 10 |
| 3 | 13.260 | 6.6716 | 4 |
| 4 | 14.100 | 6.2759 | 6 |
| 5 | 14.580 | 6.0704 | 100 |
| 6 | 16.180 | 5.4735 | 4 |
| 7 | 16.680 | 5.3106 | 4 |
| 8 | 17.560 | 5.0464 | 2 |
| 9 | 17.900 | 4.9513 | 12 |
| 10 | 18.980 | 4.6719 | 7 |
| 11 | 19.480 | 4.5531 | 2 |
| 12 | 20.580 | 4.3121 | 2 |
| 13 | 21.300 | 4.1680 | 5 |
| 14 | 21.520 | 4.1259 | 5 |
| 15 | 22.120 | 4.0153 | 1 |
| 16 | 23.660 | 3.7573 | 5 |
| 17 | 25.120 | 3.5421 | 3 |
| 18 | 26.200 | 3.3985 | 8 |
| 19 | 26.440 | 3.3682 | 17 |
| 20 | 27.100 | 3.2877 | 3 |
| 21 | 27.640 | 3.2247 | 4 |
| 22 | 28.680 | 3.1100 | 15 |
| 23 | 29.480 | 3.0274 | 9 |
| 24 | 29.780 | 2.9976 | 8 |
| 25 | 30.220 | 2.9550 | 5 |
| 26 | 31.340 | 2.8519 | 3 |
| 27 | 32.240 | 2.7743 | 4 |
| 28 | 32.540 | 2.7494 | 3 |
| 29 | 33.360 | 2.6837 | 2 |
| 30 | 34.500 | 2.5975 | 2 |
| 31 | 35.620 | 2.5184 | 3 |
| 32 | 36.160 | 2.4820 | 2 |
| 33 | 39.580 | 2.2751 | 2 |
| 34 | 40.800 | 2.2098 | 2 |
| 35 | 41.760 | 2.1612 | 2 |
| 36 | 43.060 | 2.0989 | 2 |
| 37 | 47.700 | 1.9050 | 3 |

Figure 9:
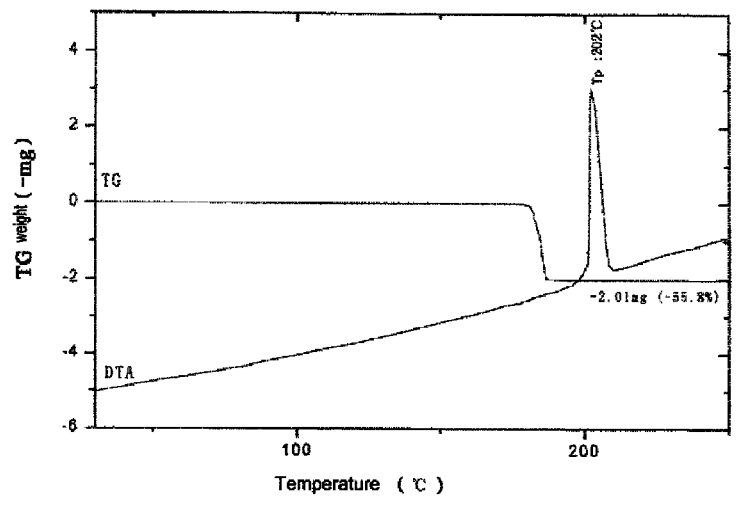
FIG. 9 is the TG-DTA chart of Form A1 prepared by using methanol as the second organic solvent.

As shown in TG-DTA spectrum, Form A1 has an exothermic peak at 202° C. (FIG. 9).

Figure 16:
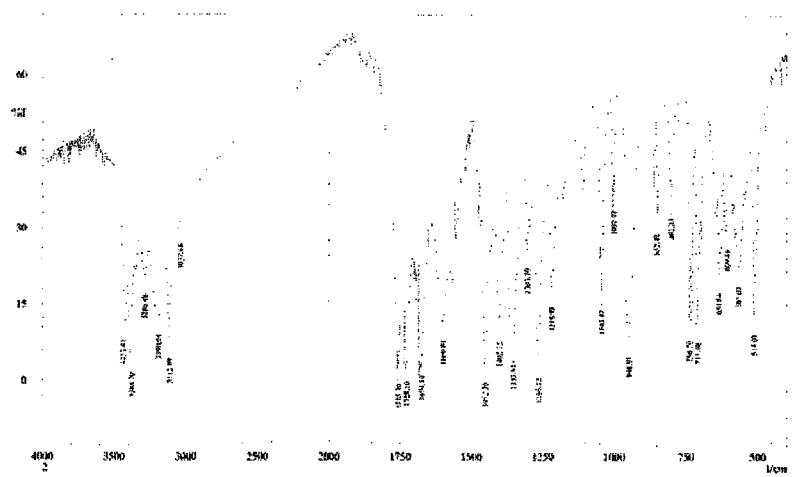
FIG. 16 is the infrared absorption spectrum of Form A1 prepared by using methanol as the second organic solvent.

As shown in infrared absorption spectrum data, Form A1 has characteristic absorption peaks at 3423.41, 3388.70, 3112.89, 1755.10, 1728.10, 1674.10, 1452.30, 1265.22 and 948.91 cm$^{-1}$ (FIG. 16).

By comparing the powder X-ray diffraction data, TG-DTA data and infrared absorption data between Form A0 and Form A1, it can be identified that both ones should be the same crystalline form, which is totally referred to as crystalline Form A.

Figure 3:
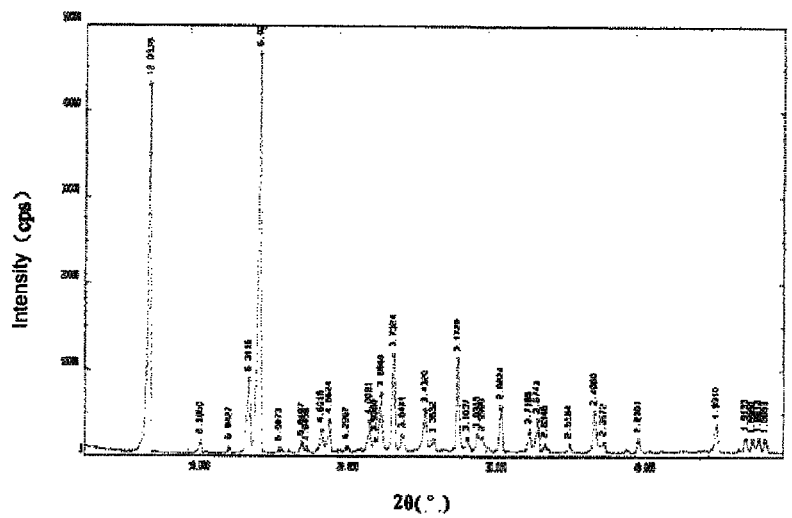
FIG. 3 is the X-ray diffraction pattern of Form B0 prepared by using isopropanol as the second organic solvent.

In another embodiment of the present invention, when the second organic solvent is isopropanol, the resultant crystalline form of Temozolomide is named as Form B0, characterized by powder X-ray diffraction spectrum comprising characteristic diffraction peaks expressed in terms of 2θ at 7.34±0.2, 14.70±0.2, 22.98±0.2, 23.82±0.2 and 28.10±0.2. Specific X-ray diffraction data are shown in Table 3 and the X-ray diffraction pattern is shown in FIG. 3.

TABLE 3

Characteristic peak parameters of X-ray diffraction pattern of Form B0

| Nos. | 2θ | d value | Relative intensity I/I₀ |
|---|---|---|---|
| 1 | 7.340 | 12.0338 | 92 |
| 2 | 10.800 | 8.1850 | 3 |
| 3 | 12.740 | 6.9427 | 2 |
| 4 | 14.020 | 6.3116 | 19 |
| 5 | 14.700 | 6.0211 | 100 |
| 6 | 16.080 | 5.5073 | 2 |
| 7 | 17.580 | 5.0407 | 3 |
| 8 | 17.920 | 4.9458 | 2 |
| 9 | 18.900 | 4.6915 | 6 |
| 10 | 19.440 | 4.5624 | 9 |
| 11 | 20.640 | 4.2997 | 2 |
| 12 | 22.160 | 4.0081 | 9 |
| 13 | 22.560 | 3.9380 | 4 |
| 14 | 22.980 | 3.8669 | 15 |
| 15 | 23.820 | 3.7324 | 25 |
| 16 | 24.420 | 3.6421 | 5 |
| 17 | 25.940 | 3.4320 | 11 |
| 18 | 26.480 | 3.3632 | 4 |
| 19 | 28.100 | 3.1729 | 24 |
| 20 | 28.740 | 3.1037 | 4 |
| 21 | 29.440 | 3.0315 | 5 |
| 22 | 29.760 | 2.9996 | 5 |
| 23 | 31.000 | 2.8824 | 12 |
| 24 | 32.920 | 2.7185 | 6 |
| 25 | 33.480 | 2.6743 | 9 |
| 26 | 34.000 | 2.6346 | 3 |
| 27 | 35.620 | 2.5184 | 3 |
| 28 | 37.360 | 2.4050 | 11 |
| 29 | 37.980 | 2.3672 | 3 |
| 30 | 40.300 | 2.2361 | 4 |
| 31 | 45.520 | 1.9910 | 8 |
| 32 | 47.480 | 1.9133 | 5 |
| 33 | 47.940 | 1.8960 | 4 |
| 34 | 48.340 | 1.8813 | 4 |
| 35 | 48.780 | 1.8653 | 4 |

Figure 10:
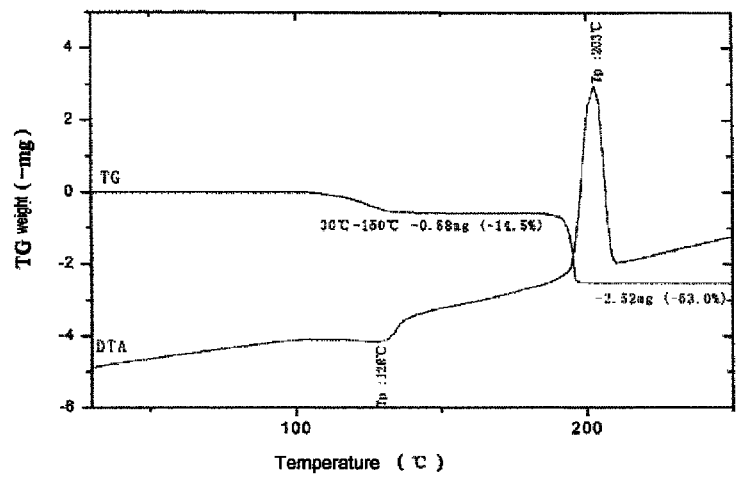
FIG. 10 is the TG-DTA chart of Form B0 prepared by using isopropanol as the second organic solvent.

As shown in TG-DTA spectrum, Form B0 has an exothermic peak at 203° C. (FIG. 10).

Figure 17:
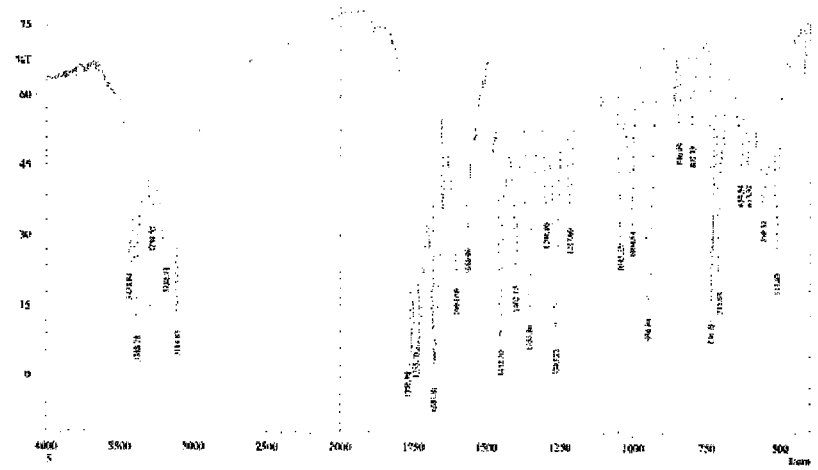
FIG. 17 is the infrared absorption spectrum of Form B0 prepared by using isopropanol as the second organic solvent.

As shown in infrared absorption spectrum data, Form B0 is characterized in that it has characteristic absorption peaks at 3388.70, 3114.82, 1758.96, 1681.81, 1452.30, 1265.22, 950.84 and 736.76 cm$^{-1}$ (FIG. 17).

Figure 4:
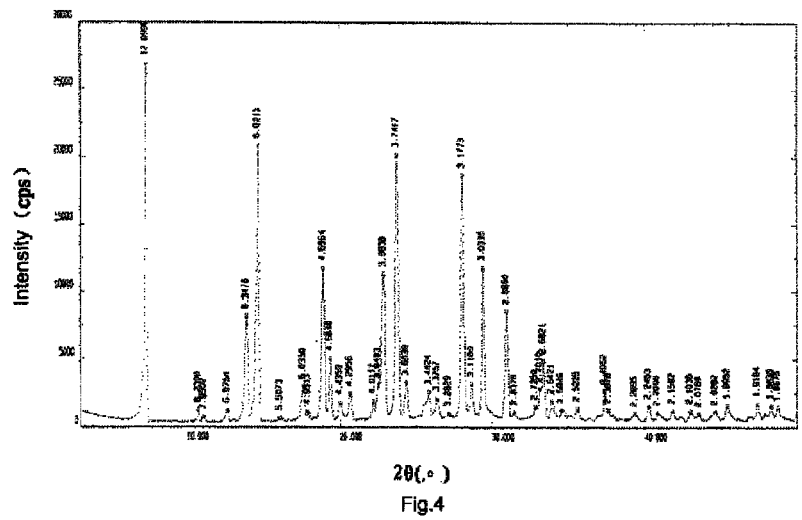
FIG. 4 is the X-ray diffraction pattern of Form B1 prepared by using acetone as the second organic solvent.

In another embodiment of the present invention, when the second organic solvent is acetone, the resultant crystalline form of Temozolomide is named as Form B1, characterized by powder X-ray diffraction spectrum comprising characteristic peaks expressed in terms of 2θ at 7.30±0.2, 14.70±0.2, 18.88±0.2, 23.76±0.2, 28.06±0.2 and 29.42±0.2. Specific X-ray diffraction data are shown in Table 4 and the X-ray diffraction pattern is shown in FIG. 4.

TABLE 4

Characteristic peak parameters of X-ray diffraction pattern of Form B1

| Nos. | 2θ | d value | Relative intensity I/I₀ |
|---|---|---|---|
| 1 | 7.300 | 12.0996 | 100 |
| 2 | 10.740 | 8.2306 | 5 |
| 3 | 11.120 | 7.9502 | 3 |
| 4 | 12.680 | 6.9754 | 5 |
| 5 | 13.940 | 6.3476 | 30 |
| 6 | 14.700 | 6.0211 | 78 |
| 7 | 16.080 | 5.5073 | 3 |
| 8 | 17.600 | 5.0350 | 11 |
| 9 | 17.900 | 4.9513 | 4 |
| 10 | 18.880 | 4.6964 | 44 |
| 11 | 19.360 | 4.5810 | 19 |
| 12 | 20.000 | 4.4359 | 7 |
| 13 | 20.660 | 4.2956 | 9 |
| 14 | 22.140 | 4.0117 | 7 |
| 15 | 22.500 | 3.9483 | 11 |
| 16 | 22.880 | 3.8836 | 42 |
| 17 | 23.760 | 3.7417 | 75 |
| 18 | 24.340 | 3.6539 | 12 |
| 19 | 25.860 | 3.4424 | 10 |
| 20 | 26.380 | 3.3757 | 8 |
| 21 | 27.140 | 3.2829 | 4 |
| 22 | 28.060 | 3.1773 | 69 |
| 23 | 28.680 | 3.1100 | 12 |
| 24 | 29.420 | 3.0335 | 44 |
| 25 | 30.960 | 2.8860 | 32 |
| 26 | 31.500 | 2.8378 | 4 |
| 27 | 32.840 | 2.7250 | 6 |
| 28 | 33.140 | 2.7010 | 10 |
| 29 | 33.380 | 2.6821 | 18 |
| 30 | 33.900 | 2.6421 | 7 |
| 31 | 34.540 | 2.5946 | 5 |
| 32 | 35.560 | 2.5225 | 5 |
| 33 | 37.340 | 2.4062 | 10 |
| 34 | 37.640 | 2.3878 | 5 |
| 35 | 39.320 | 2.2895 | 4 |
| 36 | 40.220 | 2.2403 | 6 |
| 37 | 40.800 | 2.2098 | 4 |
| 38 | 41.820 | 2.1582 | 5 |
| 39 | 42.960 | 2.1036 | 5 |
| 40 | 43.540 | 2.0769 | 4 |
| 41 | 44.640 | 2.0282 | 4 |
| 42 | 45.420 | 1.9952 | 6 |
| 43 | 47.400 | 1.9164 | 7 |
| 44 | 48.280 | 1.8835 | 6 |
| 45 | 48.720 | 1.8675 | 5 |

Figure 11:
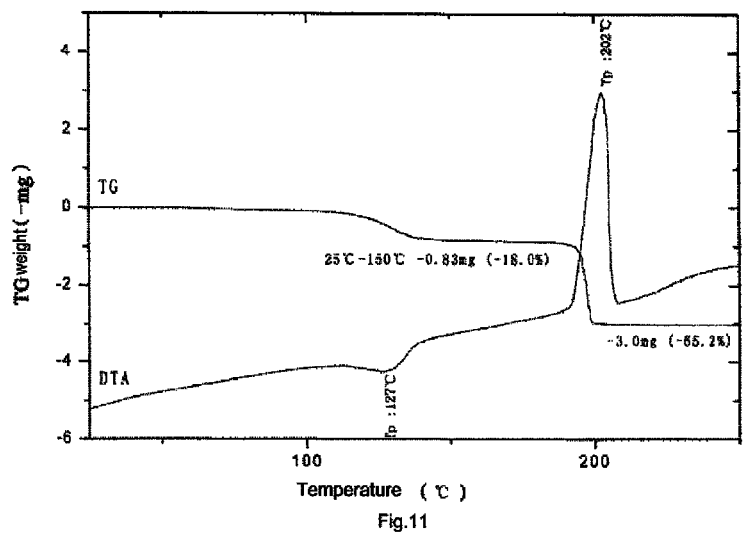
FIG. 11 is the TG-DTA chart of Form B1 prepared by using acetone as the second organic solvent.

As shown in TG-DTA spectrum, Form B1 has an exothermic peak at 202° C. (FIG. 11).

Figure 18:
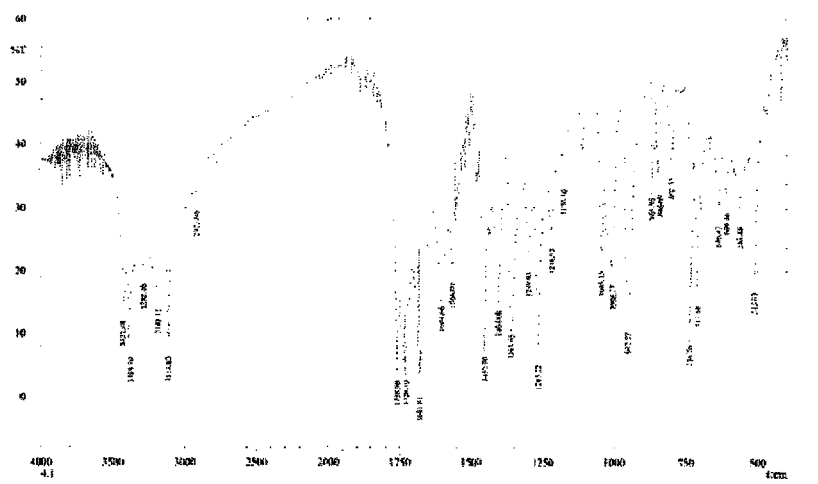
FIG. 18 is the infrared absorption spectrum of Form B1 prepared by using acetone as the second organic solvent.

As shown in infrared absorption spectrum data, Form B1 has characteristic absorption peaks at 3388.70, 3114.82, 1758.96, 1728.10, 1681.81, 1452.30, 1265.22, 952.77 and 736.76 cm$^{-1}$ (FIG. 18).

Figure 5:
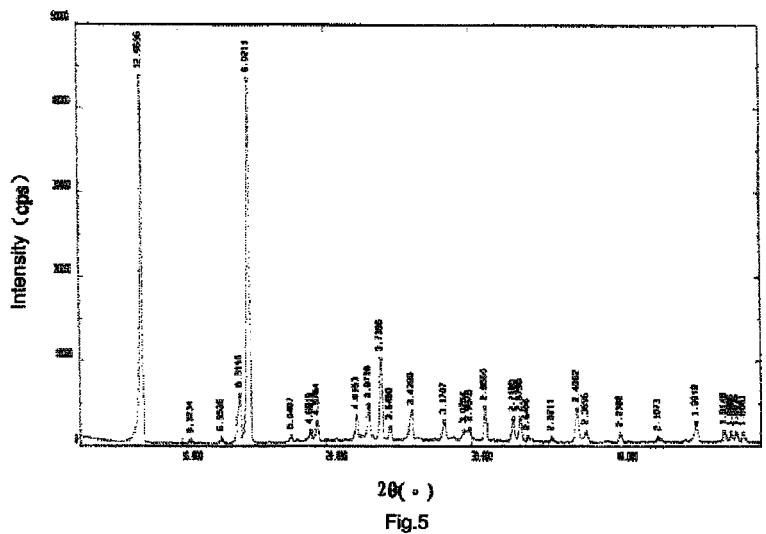
FIG. 5 is the X-ray diffraction pattern of Form B2 prepared by using dichloromethane as the second organic solvent.

In another embodiment of the present invention, when the second organic solvent is dichloromethane, the resultant crystalline form of Temozolomide is named as Form B2, characterized by powder X-ray diffraction spectrum comprising characteristic peaks expressed in terms of 2θ at 7.32±0.2, 14.02±0.2, 14.70±0.2, 22.94±0.2 and 23.78±0.2. Specific X-ray diffraction data are shown in Table 5 and the X-ray diffraction pattern is shown in FIG. 5.

TABLE 5

Characteristic peak parameters of X-ray diffraction pattern of Form B2

| Nos. | 2θ | d value | Relative intensity I/I₀ |
|---|---|---|---|
| 1 | 7.320 | 12.0666 | 100 |
| 2 | 10.620 | 8.3234 | 1 |
| 3 | 12.720 | 6.9536 | 2 |
| 4 | 14.020 | 6.3116 | 14 |
| 5 | 14.700 | 6.0211 | 99 |
| 6 | 17.580 | 5.0407 | 3 |
| 7 | 18.900 | 4.6915 | 4 |
| 8 | 19.380 | 4.5764 | 6 |
| 9 | 22.120 | 4.0153 | 8 |
| 10 | 22.940 | 3.8736 | 11 |
| 11 | 23.780 | 3.7386 | 24 |
| 12 | 24.400 | 3.6450 | 5 |
| 13 | 25.880 | 3.4398 | 9 |
| 14 | 28.120 | 3.1707 | 7 |
| 15 | 29.500 | 3.0254 | 4 |
| 16 | 29.880 | 2.9878 | 5 |
| 17 | 30.960 | 2.8860 | 10 |
| 18 | 32.920 | 2.7185 | 7 |
| 19 | 33.420 | 2.6790 | 8 |
| 20 | 33.920 | 2.6406 | 2 |
| 21 | 35.580 | 2.5211 | 2 |
| 22 | 37.340 | 2.4062 | 10 |
| 23 | 37.940 | 2.3696 | 4 |
| 24 | 40.260 | 2.2382 | 3 |
| 25 | 42.880 | 2.1073 | 2 |
| 26 | 45.500 | 1.9919 | 6 |
| 27 | 47.440 | 1.9148 | 4 |
| 28 | 47.920 | 1.8968 | 4 |
| 29 | 48.280 | 1.8835 | 4 |
| 30 | 48.760 | 1.8661 | 3 |

Figure 12:
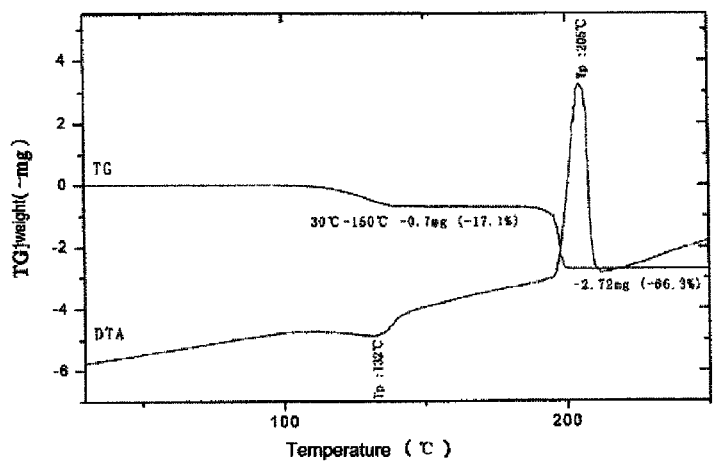
FIG. 12 is the TG-DTA chart of Form B2 prepared by using dichloromethane as the second organic solvent.

As shown in TG-DTA spectrum, Form B2 has an exothermic peak at 205° C. (FIG. 12).

Figure 19:
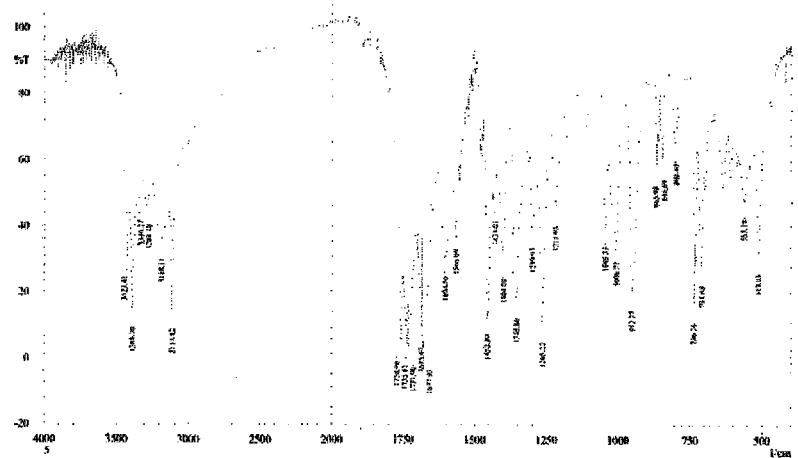
FIG. 19 is the infrared absorption spectrum of Form B2 prepared by using dichloromethane as the second organic solvent.

As shown in infrared absorption spectrum data, Form B2 has characteristic absorption peaks at 3388.70, 3114.82, 1758.96, 1735.81, 1731.96, 1677.95, 1452.30, 1265.22, 952.77 and 736.76 cm$^{-1}$ (FIG. 19).

Figure 6:
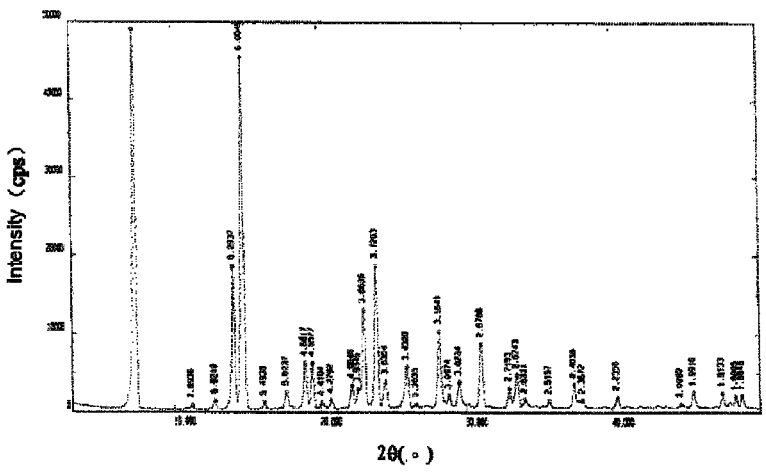
FIG. 6 is the X-ray diffraction pattern of Form B3 prepared by using ethyl acetate as the second organic solvent.

In another embodiment of the present invention, when the second organic solvent is ethyl acetate, the resultant crystalline form of Temozolomide is named as Form B3, characterized by powder X-ray diffraction spectrum comprising characteristic peaks expressed in terms of 2θ at 7.36±0.2, 14.06±0.2, 14.74±0.2, 23.00±0.2 and 23.86±0.2. Specific X-ray diffraction data are shown in Table 6 and the X-ray diffraction pattern is shown in FIG. 6.

TABLE 6

Characteristic peak parameters of X-ray diffraction pattern of Form B3

| Nos. | 2θ | d value | Relative intensity I/I₀ |
|---|---|---|---|
| 1 | 7.360 | 12.0011 | 100 |
| 2 | 11.200 | 7.8936 | 2 |
| 3 | 12.780 | 6.9210 | 3 |
| 4 | 14.060 | 6.2937 | 38 |
| 5 | 14.740 | 6.0049 | 93 |
| 6 | 16.120 | 5.4938 | 3 |
| 7 | 17.640 | 5.0237 | 5 |
| 8 | 18.940 | 4.6817 | 13 |
| 9 | 19.460 | 4.5577 | 13 |
| 10 | 20.080 | 4.4184 | 3 |
| 11 | 20.740 | 4.2792 | 3 |
| 12 | 22.180 | 4.0046 | 7 |
| 13 | 22.580 | 3.9345 | 6 |
| 14 | 23.000 | 3.8636 | 27 |
| 15 | 23.860 | 3.7263 | 38 |
| 16 | 24.500 | 3.6304 | 8 |
| 17 | 25.940 | 3.4320 | 12 |
| 18 | 26.560 | 3.3533 | 2 |
| 19 | 28.180 | 3.1641 | 21 |
| 20 | 28.800 | 3.0974 | 4 |
| 21 | 29.520 | 3.0234 | 8 |
| 22 | 31.040 | 2.8788 | 18 |
| 23 | 32.960 | 2.7153 | 6 |

TABLE 6-continued

Characteristic peak parameters of X-ray diffraction pattern of Form B3

| Nos. | 2θ | d value | Relative intensity I/I$_0$ |
|---|---|---|---|
| 24 | 33.480 | 2.6743 | 10 |
| 25 | 34.020 | 2.6331 | 3 |
| 26 | 35.660 | 2.5157 | 3 |
| 27 | 37.380 | 2.4038 | 7 |
| 28 | 37.980 | 2.3672 | 3 |
| 29 | 40.320 | 2.2350 | 4 |
| 30 | 44.640 | 2.0282 | 2 |
| 31 | 45.520 | 1.9910 | 5 |
| 32 | 47.480 | 1.9133 | 5 |
| 33 | 48.360 | 1.8805 | 4 |
| 34 | 48.800 | 1.8646 | 4 |

Figure 13:
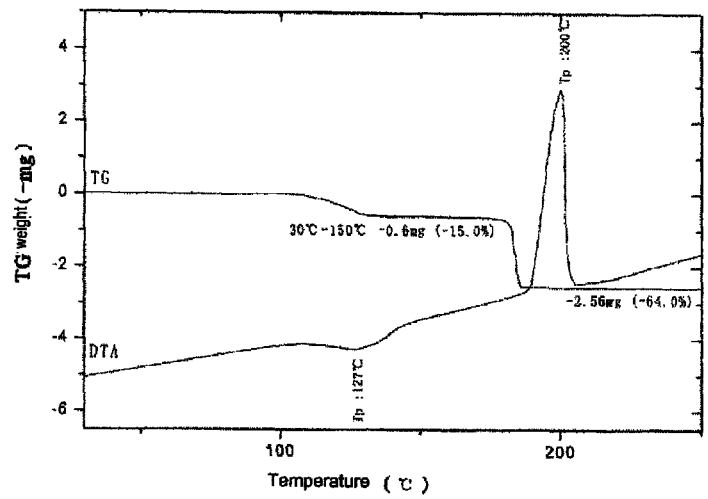
FIG. 13 is the TG-DTA chart of Form B3 prepared by using ethyl acetate as the second organic solvent.

As shown in TG-DTA spectrum, Form B3 has an exothermic peak at 200° C. (FIG. 13).

Figure 20:
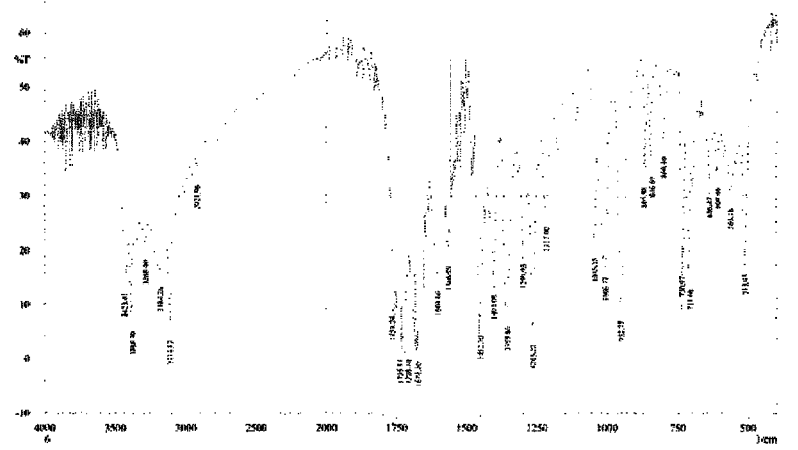
FIG. 20 is the infrared absorption spectrum of Form B3 prepared by using ethyl acetate as the second organic solvent.

As shown in infrared absorption spectrum data, Form B3 has characteristic absorption peaks at 3388.70, 3114.82, 1751.24, 1735.81, 1728.10, 1674.10, 1452.30, 1265.22, 952.77, 730.97 and 711.68 cm$^{-1}$ (FIG. 20).

By comparing the powder X-ray diffraction, TG-DTA data and infrared absorption data of B0, B1, B2 and B3 crystalline forms, it can be identified that these four ones should be the same crystalline form, which is totally referred to as crystalline Form B.

Figure 7:
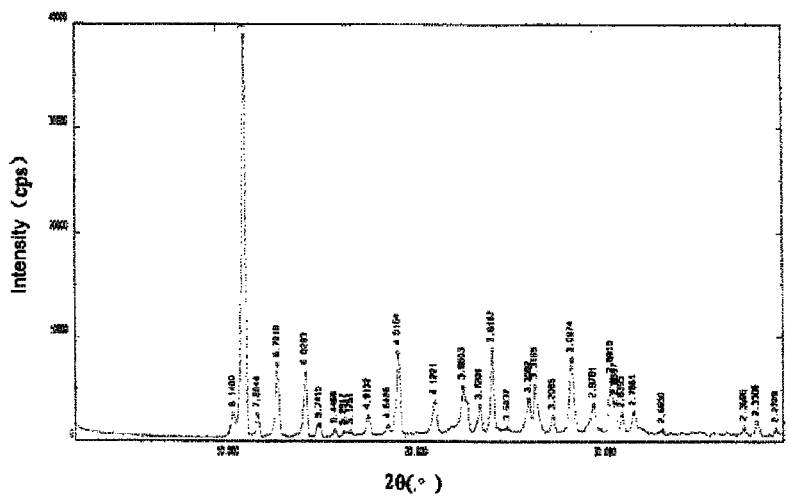
FIG. 7 is the X-ray diffraction pattern of Form C prepared by using glycol as the second organic solvent.

In another embodiment of the present invention, when the second organic solvent is glycol, the resultant crystalline form of Temozolomide is named as Form C, characterized by powder X-ray diffraction spectrum comprising characteristic peaks expressed in terms of 2θ at 11.46±0.2, 13.20±0.2, 19.64±0.2, 24.58±0.2 and 28.80±0.2. Specific X-ray diffraction data are shown in Table 7 and the X-ray diffraction pattern is shown in FIG. 7.

TABLE 7

Characteristic peak parameters of X-ray diffraction pattern of Form C

| Nos. | 2θ | d value | Relative intensity I/I$_0$ |
|---|---|---|---|
| 1 | 10.860 | 8.1400 | 7 |
| 2 | 11.460 | 7.7151 | 100 |
| 3 | 12.140 | 7.2844 | 7 |
| 4 | 13.200 | 6.7018 | 19 |
| 5 | 14.680 | 6.0293 | 17 |
| 6 | 15.420 | 5.7415 | 4 |
| 7 | 16.260 | 5.4468 | 3 |
| 8 | 16.740 | 5.2917 | 2 |
| 9 | 17.120 | 5.1751 | 3 |
| 10 | 18.040 | 4.9132 | 6 |
| 11 | 19.100 | 4.6428 | 4 |
| 12 | 19.640 | 4.5164 | 22 |
| 13 | 21.540 | 4.1221 | 10 |
| 14 | 23.020 | 3.8603 | 14 |
| 15 | 23.900 | 3.7201 | 9 |
| 16 | 24.580 | 3.6187 | 23 |
| 17 | 25.400 | 3.5037 | 4 |
| 18 | 26.520 | 3.3582 | 10 |
| 19 | 26.860 | 3.3165 | 14 |
| 20 | 27.800 | 3.2065 | 6 |
| 21 | 28.800 | 3.0974 | 20 |
| 22 | 29.980 | 2.9781 | 9 |
| 23 | 30.900 | 2.8915 | 15 |
| 24 | 31.140 | 2.8697 | 10 |
| 25 | 31.480 | 2.8395 | 7 |
| 26 | 32.100 | 2.7861 | 7 |
| 27 | 33.600 | 2.6650 | 3 |
| 28 | 37.940 | 2.3696 | 4 |
| 29 | 38.600 | 2.3306 | 5 |
| 30 | 39.620 | 2.2729 | 3 |
| 31 | 41.340 | 2.1822 | 10 |
| 32 | 43.320 | 2.0869 | 4 |

TABLE 7-continued

Characteristic peak parameters of X-ray diffraction pattern of Form C

| Nos. | 2θ | d value | Relative intensity I/I$_0$ |
|---|---|---|---|
| 33 | 43.580 | 2.0751 | 9 |
| 34 | 46.380 | 1.9561 | 4 |
| 35 | 46.920 | 1.9349 | 15 |
| 36 | 49.780 | 1.8302 | 5 |

Figure 14:
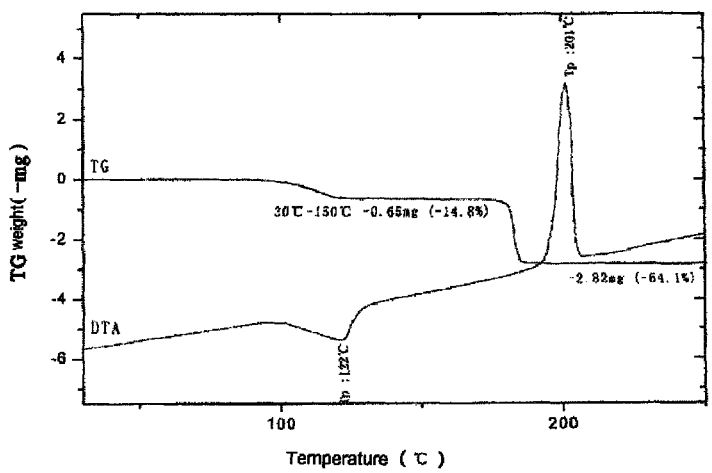
FIG. 14 is the TG-DTA chart of Form C prepared by using glycol as the second organic solvent.

As shown in TG-DTA spectrum, Form C has an exothermic peak at 201° C. (FIG. 14).

Figure 21:
FIG. 21 is the infrared absorption spectrum of Form C prepared by using glycol as the second organic solvent.

As shown in infrared absorption spectrum data, Form C has characteristic absorption peaks at 3388.70, 3112.89, 1758.96, 1731.96, 1674.10, 1454.23, 1267.14, 950.84, 736.76 and 698.18 cm$^{-1}$ (FIG. 21).

According to the second aspect, the present invention also provides a pharmaceutical composition, particularly a solid pharmaceutical composition, and the pharmaceutical composition contains any one of the crystalline forms of Temozolomide of the present invention.

The API of the pharmaceutical composition is any one of the crystalline forms of Temozolomide of the present invention, and its percentage by weight in the preparations may be 0.01-99.99%, and the balanced is pharmaceutically acceptable carrier(s).

Preferably, the solid pharmaceutical composition of the present invention is solid pharmaceutical compositions for oral administration, such as tablets, capsules, granules, pills, dry powders and the like.

The usage and dosage of the pharmaceutical compositions are determined by the patient's conditions, e.g. 1-3 times per day.

Compared with the prior art, the present invention has the following advantages:

(1) Improved yield rate: since DMSO belongs to an aprotic polar solvent, and Temozolomide has a large solubility in DMSO, only a small amount of the solvent is needed for purification. Addition of the second organic solvent can improve product yield rate greatly.

(2) Increased purity: the organic impurities in Temozolomide have a high solubility in the second organic solvent and DSMO, especially the colored allergic impurities which are difficult to be removed by other solvents can be eliminated. Thus, the product purity increases significantly.

(3) Purity and stability of the crystalline forms of Temozolomide prepared by the method of the present invention are better than those in the prior art.

The advantages of the present invention are presented by the following experimental data:

I. Solubility Test

It should be noted that each crystalline form of Form A, Form B and Form C has similar solubility properties. Hereinafter, Form A0, B0 and C were chosen only for illustrative purpose.

1. Solubility test of the crystalline Form A of Temozolomide (Form A0 prepared by the method of EXAMPLE 1). Solubility properties were assayed respectively by using DMSO, methanol, water, glacial acetic acid, 0.1M HCl, 0.1M NaOH and ethanol as the solvents. The results are shown in Table 8.

TABLE 8

Results of solubility test of crystalline Form A of Temozolomide

| Solvents | Tested drug (mg) | Amount of solvent for dissolving tested drug (ml) | Amount of solvent for dissolving 1 g of tested drug (ml) | Solubility |
|---|---|---|---|---|
| DMSO | 10.10 | 0.7 | 70 | sparingly soluble |
| Methanol | 9.98 | 7.0 | 700 | Slightly soluble |
| Water | 9.84 | 8.0 | 800 | Slightly soluble |
| Glacial acetic acid | 10.09 | 3.0 | 300 | Slightly soluble |
| 0.1M HCl | 10.13 | 7 | 700 | Slightly soluble |
| 0.1M NaOH | 9.95 | 3 | 300 | Slightly soluble |
| Ethanol | 10.03 | 55 | 5500 | Very slightly soluble |

2. Solubility test of the crystalline form B of Temozolomide (Form B0 prepared by the method of EXAMPLE 6). Solubility properties were assayed respectively by using DMSO, methanol, water, glacial acetic acid, 0.1M HCl, 0.1M NaOH and ethanol as the solvents. The results are shown in Table 9.

TABLE 9

Results of solubility test of crystalline Form B of Temozolomide

| Solvents | Tested drug (mg) | Amount of solvent for dissolving tested drug (ml) | Amount of solvent for dissolving 1 g of tested drug (ml) | Solubility |
|---|---|---|---|---|
| DMSO | 10.07 | 0.6 | 70 | sparingly soluble |
| Methanol | 9.89 | 9.0 | 900 | Slightly soluble |
| Water | 10.02 | 8.0 | 800 | Slightly soluble |
| Glacial acetic acid | 9.99 | 3.0 | 300 | Slightly soluble |
| 0.1M HCl | 9.93 | 8 | 800 | Slightly soluble |
| 0.1M NaOH | 10.05 | 3 | 300 | Slightly soluble |
| Ethanol | 10.13 | 57 | 5700 | Very slightly soluble |

3. Solubility test of the crystalline form C of Temozolomide (Form C prepared by the method of EXAMPLE 14). Solubility properties were assayed respectively by using DMSO, methanol, water, glacial acetic acid, 0.1M HCl, 0.1M NaOH and ethanol as the solvents. The results are shown in Table 10.

TABLE 10

Results of solubility test of crystalline Form C of Temozolomide

| Solvents | Tested drug (mg) | Amount of solvent for dissolving tested drug (ml) | Amount of solvent for dissolving 1 g of tested drug (ml) | Solubility |
|---|---|---|---|---|
| DMSO | 9.95 | 0.8 | 80 | sparingly soluble |
| Methanol | 9.91 | 8.0 | 800 | Slightly soluble |
| Water | 10.08 | 8.0 | 800 | Slightly soluble |
| Glacial acetic acid | 10.21 | 3.0 | 300 | Slightly soluble |
| 0.1M HCl | 10.11 | 8.0 | 800 | Slightly soluble |
| 0.1M NaOH | 9.97 | 3.0 | 300 | Slightly soluble |
| Ethanol | 10.17 | 60 | 6000 | Very slightly soluble |

II. Stability Test

In the following test, related substances were determined as follows: HPLC method was used and chromatographic conditions were as follows: C18 column using octadecylsilane bonded silica gel as the filler, isocratic elution using methanol: 0.5% glacial acetic acid solution (10:90) as the mobile phase, and detection wavelength was at 254 nm.

It should be noted that each crystalline form of Form A, Form B and Form C has similar stability properties. Hereinafter, Form A0, Form B0 and Form C were chosen only for illustrative purpose.

1. Stability of Crystalline Form A of Temozolomide
1.1 Light Exposure Test

Crystalline form A of Temozolomide (Form A0 prepared by the method of EXAMPLE 1) was exposed under conditions of light intensity of 4500±500Lx, sampled and determined on the 5$^{th}$ and 10$^{th}$ day. The results are shown in Table 11.

TABLE 11

Results of crystalline Form A of Temozolomide in the strong light exposure test

| Time (day) | Appearance and color | Drying loss (%) | Content (%) | Related substances |
|---|---|---|---|---|
| 0$^{th}$ day | White powder | 0.35 | 99.94 | Not detected |
| 5$^{th}$ day | White powder | 0.33 | 99.93 | Not detected |
| 10$^{th}$ day | White powder | 0.39 | 99.81 | Not detected |

1.2 High Temperature Test

Crystalline form A of Temozolomide (Form A0 prepared by the method of EXAMPLE 1) was placed in 60° C. incubator, sampled and determined on the 5$^{th}$ and 10$^{th}$ day. The results are shown in Table 12.

TABLE 12

Results of crystalline Form A of Temozolomide in the high temperature test

| Time (day) | Appearance and color | Drying loss (%) | Content (%) | Related substances |
|---|---|---|---|---|
| 0$^{th}$ day | White powder | 0.41 | 99.94 | Not detected |
| 5$^{th}$ day | White powder | 0.38 | 99.63 | Not detected |
| 10$^{th}$ day | White powder | 0.34 | 99.31 | Not detected |

1.3 High Humidity Test

Crystalline Form A of Temozolomide (Form A0 prepared by the method of EXAMPLE 1) was placed in 25° C. incubator (relative humidity: 75±5%), sampled and determined on the 5$^{th}$ and 10$^{th}$ day. The results are shown in Table 13.

TABLE 13

Results of crystalline Form A of Temozolomide in the high humidity test

| Time (day) | Appearance and color | Weight gain of moisture absorption (%) | Content (%) | Related substances |
|---|---|---|---|---|
| 0$^{th}$ day | White powder | 0 | 99.94 | Not detected |
| 5$^{th}$ day | White powder | 0.32 | 99.73 | Not detected |
| 10$^{th}$ day | White powder | 0.51 | 99.52 | Not detected |

1.4 Accelerated Test

Crystalline Form A of Temozolomide (Form A0 prepared by the method of EXAMPLE 1) was sealed by a polyethylene film bag, placed under conditions of 40±2° C. and a relative humidity of 75±5% for 6 months, sampled and determined at the end of the $1^{st}, 2^{nd}, 3^{rd}$ and $6^{th}$ month. The results are shown in Table 14.

TABLE 14

Results of crystalline Form A of Temozolomide in the accelerated test

| Time | Appearance and color | Content (%) | Related substances |
|---|---|---|---|
| $0^{th}$ month | White powder | 99.94 | Not detected |
| $1^{st}$ month | White powder | 99.81 | Not detected |
| $2^{nd}$ month | White powder | 99.64 | Not detected |
| $3^{rd}$ month | White powder | 99.92 | Not detected |
| $6^{th}$ month | White powder | 99.62 | Not detected |

As shown in the results, crystalline Form A of Temozolomide was stable in the light exposure test, the high-temperature test, the high-humidity test and the accelerated test, and there was no obvious change in the appearance and color, the drying loss, the content and the related substances. The weight gain of moisture absorption slightly increased under the high-humidity condition.

2. Stability of Crystalline Form B of Temozolomide 2.1 Light Exposure Test

Crystalline form B of Temozolomide (Form B0 prepared by the method of EXAMPLE 6) was placed, exposed under conditions of light intensity of 4500±500Lx, sampled and determined on the $5^{th}$ and $10^{th}$ day. The results are shown in Table 15.

TABLE 15

Results of crystalline Form B of Temozolomide in the strong light exposure test

| Time (day) | Appearance and color | Drying loss (%) | Content (%) | Related substances |
|---|---|---|---|---|
| $0^{th}$ day | White powder | 0.38 | 99.97 | Not detected |
| $5^{th}$ day | White powder | 0.33 | 99.92 | Not detected |
| $10^{th}$ day | White powder | 0.29 | 99.95 | Not detected |

2.2 High Temperature Test

Crystalline Form B of Temozolomide (Form B0 prepared by the method of EXAMPLE 6) was placed in 60° C. incubator, sampled and determined on the $5^{th}$ and $10^{th}$ day. The results are shown in Table 16.

TABLE 16

Results of crystalline Form B of Temozolomide in the high temperature test

| Time (day) | Appearance and color | Drying loss (%) | Content (%) | Related substances |
|---|---|---|---|---|
| $0^{th}$ day | White powder | 0.33 | 99.97 | Not detected |
| $5^{th}$ day | White powder | 0.27 | 99.73 | Not detected |
| $10^{th}$ day | White powder | 0.29 | 99.61 | Not detected |

2.3 High Humidity Test

Crystalline Form B of Temozolomide (Form B0 prepared by the method of EXAMPLE 6) was placed in 25° C. incubator (relative humidity: 75±5%), sampled and determined on the $5^{th}$ and $10^{th}$ day. The results are shown in Table 17.

TABLE 17

Results of crystalline Form B of Temozolomide in the high humidity test

| Time (day) | Appearance and color | Weight gain of moisture absorption (%) | Content (%) | Related substances |
|---|---|---|---|---|
| $0^{th}$ day | White powder | 0 | 99.97 | Not detected |
| $5^{th}$ day | White powder | 0.37 | 99.63 | Not detected |
| $10^{th}$ day | White powder | 0.52 | 99.57 | Not detected |

2.4 Accelerated Test

Crystalline Form B of Temozolomide (Form B0 prepared by the method of EXAMPLE 6) was sealed with a polyethylene film bag and placed under conditions of 40±2° C. and a relative humidity of 75±5% for 6 months, sampled and determined at the end of the $1^{st}, 2^{nd}, 3^{rd}$ and $6^{th}$ month. The results are shown in Table 18.

TABLE 18

Results of crystalline Form B of Temozolomide in the accelerated test

| Time | Appearance and color | Content (%) | Related substances |
|---|---|---|---|
| $0^{th}$ month | White powder | 99.97 | Not detected |
| $1^{st}$ month | White powder | 99.71 | Not detected |
| $2^{nd}$ month | White powder | 99.82 | Not detected |
| $3^{rd}$ month | White powder | 99.73 | Not detected |
| $6^{th}$ month | White powder | 99.85 | Not detected |

As shown in the results, crystalline Form B of Temozolomide was stable in the light exposure test, the high-temperature, the high-humidity test and the accelerated test, and there was no obvious change in the appearance and color, the drying loss, the content and the related substances. The weight gain of moisture absorption slightly increased under the high-humidity condition.

3. Stability of Crystalline Form C of Temozolomide 3.1 Light Exposure Test

Crystalline Form C of Temozolomide (Form C prepared by the method of EXAMPLE 14) was placed, exposed under conditions of light intensity of 4500±500Lx, sampled and determined on the $5^{th}$ and $10^{th}$ day. The results are shown in Table 19.

TABLE 19

Results of crystalline Form C of Temozolomide in the strong light exposure test

| Time (day) | Appearance and color | Drying loss (%) | Content (%) | Related substances |
|---|---|---|---|---|
| $0^{th}$ day | White powder | 0.27 | 99.91 | Not detected |
| $5^{th}$ day | White powder | 0.30 | 99.90 | Not detected |
| $10^{th}$ day | White powder | 0.32 | 99.96 | Not detected |

3.2 High Temperature Test

Crystalline Form C of Temozolomide (Form C prepared by the method of EXAMPLE 14) was placed in 60° C. incubator, sampled and determined on the $5^{th}$ and $10^{th}$ day. The results are shown in Table 20.

TABLE 20

Results of crystalline Form C of Temozolomide in the high temperature test

| Time (day) | Appearance and color | Drying loss (%) | Content (%) | Related substances |
|---|---|---|---|---|
| 0th day | White powder | 0.35 | 99.91 | Not detected |
| 5th day | White powder | 0.37 | 99.79 | Not detected |
| 10th day | White powder | 0.34 | 99.69 | Not detected |

3.3 High Humidity Test

Crystalline Form C of Temozolomide (Form C prepared by the method of EXAMPLE 14) was placed in 25° C. incubator (relative humidity: 75±5%), sampled and determined on the 5$^{th}$ and 10$^{th}$ day. The results are shown in Table 21.

TABLE 21

Results of crystalline Form C of Temozolomide in the high humidity test

| Time (day) | Appearance and color | Weight gain of moisture absorption (%) | Content (%) | Related substances |
|---|---|---|---|---|
| 0th day | White powder | 0 | 99.91 | Not detected |
| 5th day | White powder | 0.29 | 99.85 | Not detected |
| 10th day | White powder | 0.47 | 99.63 | Not detected |

3.4 Accelerated Test

Crystalline Form C of Temozolomide (Form C prepared by the method of EXAMPLE 14) was sealed with a polyethylene film bag and placed under conditions of 40±2° C. and a relative humidity of 75±5% for 6 months, sampled and determined at the end of the 1$^{st}$, 2$^{nd}$, 3$^{rd}$ and 6$^{th}$ month. The results are shown in Table 22.

TABLE 22

Results of crystalline Form C of Temozolomide in the accelerated test

| Time | Appearance and color | Content (%) | Related substances |
|---|---|---|---|
| 0th month | White powder | 99.91 | Not detected |
| 1st month | White powder | 99.61 | Not detected |
| 2nd month | White powder | 99.87 | Not detected |
| 3rd month | White powder | 99.93 | Not detected |
| 6th month | White powder | 99.65 | Not detected |

As shown in the results, crystalline Form C of Temozolomide was stable in the light exposure test, the high-temperature, the high-humidity test and the accelerated test, and there was no obvious change in the appearance and color, the drying loss, the content and the related substances. The weight gain of moisture absorption slightly increased under the high-humidity condition.

EXAMPLES

The following examples were used to further illustrate the present invention. The method in the examples of the present invention are merely illustrative of the present invention and are not intended to limit the present invention.

Example 1

Preparation of Crystalline Form A of Temozolomide 20 g of Temozolomide was placed into a reaction bottle, into which 200 ml of DMSO was added, the mixture of Temozolomide and DMSO was stirred and heated to 80° C. to make the Temozolomide dissolved. 300 ml of ethanol was added, stirred for 5 min and cooled down to 10-15° C., crystallized for 4 hours by stirring to give the crystalline form. The resultant crystalline form was filtered, washed with 40 ml of ethanol and dried for 4 hours in vacuum (vacuum degree≤−0.07 Mpa) at 45-50° C. to obtain crystalline Form A0 of Temozolomide (16.4 g). The yield rate was 82%.

Example 2

Preparation of Crystalline Form A of Temozolomide 20 g of Temozolomide was placed into a reaction bottle, into which 140 ml of DMSO was added, the mixture of Temozolomide and DMSO was stirred and heated to 140° C. to make the Temozolomide dissolved. 140 ml of ethanol was added, stirred for 5 min and cooled down to 10-15° C., crystallized for 4 hours by stirring to give the crystalline form. The resultant crystalline form was filtered, washed with 60 ml of ethanol and dried for 4 hours in vacuum (vacuum degree≤−0.07 Mpa) at 45-50° C. to obtain crystalline Form A0 of Temozolomide (16.0 g). The yield rate was 80%.

Example 3

Preparation of Crystalline Form A of Temozolomide 20 g of Temozolomide was placed into a reaction bottle, into which 300 ml of DMSO was added, the mixture of Temozolomide and DMSO was stirred and heated to 60° C. to make the Temozolomide dissolved. 400 ml of ethanol was added, stirred for 5 min and cooled down to 10-15° C., crystallized for 4 hours by stirring to give the crystalline form. The resultant crystalline form was filtered, washed with 100 ml of ethanol and dried for 4 hours in vacuum (vacuum degree≤−0.07 Mpa) at 45-50° C. to obtain crystalline Form A0 of Temozolomide (16.6 g). The yield rate was 83%.

Example 4

Preparation of Crystalline Form A of Temozolomide 20 g of Temozolomide was placed into a reaction bottle, into which 140 ml of DMSO was added, the mixture of Temozolomide and DMSO was stirred and heated to 120° C. to make the Temozolomide dissolved. 100 ml of methanol was added, stirred for 10 min and cooled down to 10-15° C., crystallized for 4 hours by stirring to give the crystalline form. The resultant crystalline form was filtered, washed with 40 ml of methanol and dried for 4 hours in vacuum (vacuum degree≤−0.07 Mpa) at 45-50° C. to obtain crystalline Form A1 of Temozolomide (16.7 g). The yield rate was 83.5%.

Example 5

Preparation of Crystalline Form A of Temozolomide 20 g of Temozolomide was placed into a reaction bottle, into which 160 ml of DMSO was added, the mixture of Temozolomide and DMSO was stirred and heated to 110° C. to make the Temozolomide dissolved. 140 ml of methanol was added, stirred for 10 min and cooled down to 10-15° C., crystallized for 4 hours by stirring to give the crystalline form. The resultant crystalline form was filtered, washed with 60 ml of methanol and dried for 4 hours in vacuum (vacuum degree≤−0.07 Mpa) at 45-50° C. to obtain crystalline Form A1 of Temozolomide (16.0 g). The yield rate was 80%.

Example 6

Preparation of Crystalline Form B of Temozolomide 10 g of Temozolomide was placed into a reaction bottle, into which 80 ml of DMSO was added, the mixture of Temozolomide and DMSO was stirred and heated to 110° C. to make the Temozolomide dissolved. 200 ml of isopropanol was added, stirred for 5 min and cooled down to 10-15° C., crystallized for 4 hours by stirring to give the crystalline form. The resultant crystalline form was filtered, washed with 30 ml of isopropanol and dried for 4 hours in vacuum (vacuum degrees≤−0.07 Mpa) at 45-50° C. to obtain crystalline Form B0 of Temozolomide (9.45 g). The yield rate was 94.5%.

Example 7

Preparation of Crystalline Form B of Temozolomide 10 g of Temozolomide was placed into a reaction bottle, into which 110 ml of DMSO was added, the mixture of Temozolomide and DMSO was stirred and heated to 80° C. to make the Temozolomide dissolved. 300 ml of isopropanol was added, stirred for 5 min and cooled down to 10-15° C., crystallized for 4 hours by stirring to give the crystalline form. The resultant crystalline form was filtered, washed with 20 ml of isopropanol and dried for 4 hours in vacuum (vacuum degree≤−0.07 Mpa) at 45-50° C. to obtain crystalline Form B0 of Temozolomide (9.21 g). The yield rate was 92.1%.

Example 8

Preparation of Crystalline Form B of Temozolomide 5 g of Temozolomide was placed into a reaction bottle, into which 100 ml of DMSO was added, the mixture of Temozolomide and DMSO was stirred and heated to 60° C. to make the Temozolomide dissolved. 150 ml of acetone was added, stirred for 5 min and cooled down to 10-15° C., crystallized for 4 hours by stirring to give the crystalline form. The resultant crystalline form was filtered, washed with 50 ml of acetone and dried for 4 hours in vacuum (vacuum degree≤−0.07 Mpa) at 45-50° C. to obtain crystalline Form B1 of Temozolomide (4.1 g). The yield rate was 82%.

Example 9

Preparation of Crystalline Form B of Temozolomide 5 g of Temozolomide was placed into a reaction bottle, into which 60 ml DMSO was added, the mixture of Temozolomide and DMSO was stirred and heated to 70° C. to make the Temozolomide dissolved. 100 ml of acetone was added, stirred for 5 min and cooled down to 10-15° C., crystallized for 4 hours by stirring to give the crystalline form. The resultant crystalline form was filtered, washed with 40 ml of acetone and dried for 4 hours in vacuum (vacuum degree≤−0.07 Mpa) at 45-50° C. to obtain crystalline Form B1 of Temozolomide (4.0 g). The yield rate was 80%.

Example 10

Preparation of Crystalline Form B of Temozolomide 20 g of Temozolomide was placed into a reaction bottle, into which 250 ml of DMSO was added, the mixture of Temozolomide and DMSO was stirred and heated to 80° C. to make the Temozolomide dissolved. 300 ml of dichloromethane was added, stirred for 5 min and cooled down to 10-15° C., crystallized for 4 hours by stirring to give the crystalline form. The resultant crystalline form was filtered, washed with 50 ml of dichloromethane and dried for 4 hours in vacuum (vacuum degree≤−0.07 Mpa) at 45-50° C. to obtain crystalline Form B2 of Temozolomide (19.1 g). The yield rate was 95.5%.

Example 11

Preparation of Crystalline Form B of Temozolomide 20 g of Temozolomide was placed into a reaction bottle, into which 200 ml of DMSO was added, the mixture of Temozolomide and DMSO was stirred and heated to 80° C. to make the Temozolomide dissolved. 250 ml of dichloromethane was added, stirred for 5 min and cooled down to 10-15° C., crystallized for 4 hours by stirring to give the crystalline form. The resultant crystalline form was filtered, washed with 60 ml of dichloromethane and dried for 4 hours in vacuum (vacuum degrees≤−0.07 Mpa) at 45-50° C. to obtain crystalline Form B2 of Temozolomide (19.0 g). The yield rate was 95%.

Example 12

Preparation of Crystalline Form B of Temozolomide 10 g of Temozolomide was placed into a reaction bottle, into which 80 ml of DMSO was added, the mixture of Temozolomide and DMSO was stirred and heated to 130° C. to make the Temozolomide dissolved. 200 ml of ethyl acetate was added, stirred for 5min and cooled down to 10-15° C., crystallized for 4 hours by stirring to give the crystalline form. The resultant crystalline form was filtered, washed with 50 ml of ethyl acetate and dried for 4 hours in vacuum (vacuum degree≤−0.07 Mpa) at 45-50° C. to obtain crystalline Form B3 of Temozolomide (8.2 g). The yield rate was 82%.

Example 13

Preparation of Crystalline Form B of Temozolomide 10 g of Temozolomide was placed into a reaction bottle, into which 90 ml of DMSO was added, the mixture of Temozolomide and DMSO was stirred and heated to 110° C. to make the Temozolomide dissolved. 150 ml of ethyl acetate was added, stirred for 5 min and cooled down to 10-15° C., crystallized for 4 hours by stirring to give the crystalline form. The resultant crystalline form was filtered, washed with 40 ml of ethyl acetate and dried for 4 hours in vacuum (vacuum degree$\leq$−0.07 Mpa) at 45-50° C. to obtain crystalline Form B3 of Temozolomide (8.0 g). The yield rate was 80%.

Example 14

Preparation of Crystalline Form C of Temozolomide 20 g of Temozolomide was placed into a reaction bottle, into which 150 ml of DMSO was added, the mixture of Temozolomide and DMSO was stirred and heated to 120° C. to make the Temozolomide dissolved. 150 ml of glycol was added, stirred for 15 min and cooled down to 10-15° C., crystallized for 4 hours by stirring to give the crystalline form. The resultant crystalline form was filtered, washed with 50 ml of glycol and dried for 4 hours in vacuum (vacuum degree$\leq$−0.07 Mpa) at 45-50° C. to obtain crystalline Form C of Temozolomide (18 g). The yield rate was 90%.

Example 15

Preparation of Crystalline Form C of Temozolomide 20 g of Temozolomide was placed into a reaction bottle, into which 180 ml of DMSO was added, the mixture of Temozolomide and DMSO was stirred and heated to 100° C. to make the Temozolomide dissolved. 200 ml of glycol was added, stirred for 15 min and cooled down to 10-15° C., crystallized for 4 hours by stirring to give the crystalline form. The resultant crystalline form was filtered, washed with 70 ml of glycol and dried for 4 hours in vacuum (vacuum degree$\leq$−0.07 Mpa) at 45-50° C. to obtain crystalline Form C of Temozolomide (17.6 g). The yield rate was 88%.

Example 16

Preparation of Pharmaceutical Composition as Capsules Containing Crystalline Form A of Temozolomide (represented by Form A0 prepared by using the method of EXAMPLE 1)

1. Formulation:

| | |
|---|---|
| Specification: | 5 mg |
| Crystalline Form A of Temozolomide | 5 g |
| Lactose | 72 g |
| Microcrystalline cellulose | 15 g |
| Corn starch | 65 g |
| Sodium carboxymethyl starch | 5 g |
| Polyvinylpyrrolidone (PVP) | proper amount |
| Magnesium stearate | 1 g |
| | 1000 capsules |

2. Preparation of Capsules:

Crystalline Form A of Temozolomide, lactose, microcrystalline cellulose, corn starch and sodium carboxymethyl starch were loaded into a high-efficient wetting granulator to mix, into which 2% PVP ethanol solution (80%) was added to granulate. Resultant wet granules were dried in a fluidized bed and sized with an 18-mesh sifter, and the obtained dried granules were added with magnesium stearate, properly mixed and loaded into capsules.

Example 17

Preparation of Pharmaceutical Composition as Capsules Containing Crystalline Form B of Temozolomide (represented by Form B0 prepared by using the method of EXAMPLE 6)

1. Formulation:

| | |
|---|---|
| Specification: | 50 mg |
| Crystalline Form B of Temozolomide | 50 g |
| Lactose | 50 g |
| Microcrystalline cellulose | 10 g |
| Corn starch | 47 g |
| Sodium carboxymethyl starch | 5 g |
| Polyvinylpyrrolidone (PVP) | proper amount |
| Magnesium stearate | 1 g |
| | 1000 capsules |

2. Preparation of Capsules:

Crystalline Form B of Temozolomide, lactose, microcrystalline cellulose, corn starch and sodium carboxymethyl starch were loaded into a high-efficient wetting granulator to mix, into which 2% PVP ethanol solution (80%) was added to granulate. Resultant wet granules were dried in a fluidized bed and sized with an 18-mesh sifter, and the obtained dried granules were added with magnesium stearate, properly mixed and loaded into capsules.

Example 18

Preparation of Pharmaceutical Composition as Capsules Containing Crystalline Form C of Temozolomide (represented by Form C prepared by using the method of EXAMPLE 14)

1. Formulation:

| | |
|---|---|
| Specification: | 50 mg |
| Crystalline Form C of Temozolomide | 50 g |
| Lactose | 50 g |
| Microcrystalline cellulose | 10 g |
| Corn starch | 47 g |
| Sodium carboxymethyl starch | 5 g |
| Polyvinylpyrrolidone (PVP) | proper amount |
| Magnesium stearate | 1 g |
| | 1000 capsules |

2. Preparation of Capsules:

Crystalline Form C of Temozolomide, lactose, microcrystalline cellulose, corn starch and sodium carboxymethyl starch were loaded into a high-efficient wetting granulator to mix, into which 2% PVP ethanol solution (80%) was added to granulate. Resultant wet granules were dried in a fluidized bed and sized with an 18-mesh sifter, and the obtained dried granules were added with magnesium stearate, properly mixed and loaded into capsules.

What is claimed is:

1. A method for preparing crystalline forms of Temozolomide, characterized in that, the method consists of the following steps: dissolving Temozolomide in dimethylsulfoxide, into which a second organic solvent is added for recrystallization, whereby the crystalline forms of Temozolomide are prepared, wherein the second organic solvent is methanol, isopropanol, dichloromethane, ethyl acetate or ethylene glycol.

2. The method according to claim 1, wherein the method comprises the following steps: Temozolomide is prepared, into which dimethylsulfoxide with 7-20 times the amount of the Temozolomide (v/w) is added, the mixture of Temozolomide and dimethylsulfoxide is stirred and heated to make the Temozolomide dissolved, then the second organic solvent with 5-30 times the amount of the Temozolomide (v/w) is added, stirred, cooled down, crystallized by stirring, filtered to give the crystalline forms, and the resultant crystalline forms are washed by using the second organic solvent with 2-10 times the amount of the Temozolomide (v/w), and dried in vacuum to give the crystalline forms of Temozolomide.

3. The method according to claim 1, wherein the method comprises the following steps: Temozolomide is prepared, into which dimethylsulfoxide with 7-15 times the amount of the Temozolomide (v/w) is added, the mixture of Temozolomide and dimethylsulfoxide is stirred and heated to 60-140° C. to make the Temozolomide dissolved, then the second organic solvent with 7-20 times the amount of the Temozolomide (v/w) is added, stirred for 5-15min, cooled down to 10-15° C., crystallized for 4 hours by stirring, filtered to give the crystalline forms, and the resultant crystalline forms are washed by using the second organic solvent with 2-5 times the amount of the Temozolomide (v/w), and dried in vacuum to give the crystalline forms of Temozolomide.

4. The method according to claim 1, wherein the second organic solvent is methanol, the obtained crystalline form of Temozolomide has a powder X-ray diffraction spectrum comprising characteristic peaks expressed in terms of 2θ at 10.72±0.2, 14.58±0.2, 17.90±0.2, 26.44±0.2 and 28.68±0.2; it has characteristic absorption peaks at 3423.41, 3388.70, 3112.89, 1755.10, 1728.10, 1674.10, 1452.30, 1265.22 and 948.91 cm$^{-1}$ in its infrared absorption spectrum; and it has an exothermic peak at 202° C. in its TG-DTA spectrum.

5. The method according to claim 1, wherein the second organic solvent is isopropanol, the obtained crystalline form of Temozolomide has a powder X-ray diffraction spectrum comprising characteristic peaks expressed in terms of 2θ at 7.34±0.2, 14.70±0.2, 22.98±0.2, 23.82±0.2 and 28.10±0.2; it has characteristic absorption peaks at 3388.70, 3114.82, 1758.96, 1681.81, 1452.30, 1265.22, 950.84 and 736.76cm$^{-1}$ in its infrared absorption spectrum; and it has an exothermic peak at 203° C. in its TG-DTA spectrum.

6. The method according to claim 1, wherein the second organic solvent is dichloromethane; the obtained crystalline form of Temozolomide has a powder X-ray diffraction spectrum comprising characteristic peaks expressed in terms of 2θ at 7.32±0.2, 14.02±0.2, 14.70±0.2, 22.94±0.2 and 23.78±0.2; it has characteristic absorption peaks at 3388.70, 3114.82, 1758.96, 1735.81, 1731.96, 1677.95, 1452.30, 1265.22, 952.77 and 736.76cm$^{-1}$ in its infrared absorption spectrum; and it has an exothermic peak at 205° C. in its TG-DTA spectrum.

7. The method according to claim 1, wherein the second organic solvent is ethyl acetate; the obtained crystalline form of Temozolomide has a powder X-ray diffraction spectrum comprising characteristic peaks expressed in terms of 2θ at 7.36±0.2, 14.06±0.2, 14.74±0.2, 23.00±0.2 and 23.86±0.2; it has characteristic absorption peaks at 3388.70, 3114.82, 1751.24, 1735.81, 1728.10, 1674.10, 1452.30, 1265.22, 952.77, 730.97 and 711.68cm$^{-1}$ in its infrared absorption spectrum; and it has an exothermic peak at 200° C. in its TG-DTA spectrum.

8. The method according to claim 1, wherein the second organic solvent is ethylene glycol; the obtained crystalline form of Temozolomide has a powder X-ray diffraction spectrum comprising characteristic peaks expressed in terms of 2θ at 11.46±0.2, 13.20±0.2, 19.64±0.2, 24.58±0.2 and 28.80±0.2; it has characteristic absorption peaks at 3388.70, 3112.89, 1758.96, 1731.96, 1674.10, 1454.23, 1267.14, 950.84, 736.76 and 698.18cm$^{-1}$ in its infrared absorption spectrum; and it has an exothermic peak at 201° C. in its TG-DTA spectrum.

9. The crystalline form of Temozolomide prepared by the method of claim 8 having a powder X-ray diffraction spectrum with characteristic diffraction peaks as follows:

| Nos. | 2θ | d value | Relative intensity I/I$_0$ |
| --- | --- | --- | --- |
| 1 | 10.860 | 8.1400 | 7 |
| 2 | 11.460 | 7.7151 | 100 |
| 3 | 12.140 | 7.2844 | 7 |
| 4 | 13.200 | 6.7018 | 19 |
| 5 | 14.680 | 6.0293 | 17 |
| 6 | 15.420 | 5.7415 | 4 |
| 7 | 16.260 | 5.4468 | 3 |
| 8 | 16.740 | 5.2917 | 2 |
| 9 | 17.120 | 5.1751 | 3 |
| 10 | 18.040 | 4.9132 | 6 |
| 11 | 19.100 | 4.6428 | 4 |
| 12 | 19.640 | 4.5164 | 22 |
| 13 | 21.540 | 4.1221 | 10 |
| 14 | 23.020 | 3.8603 | 14 |
| 15 | 23.900 | 3.7201 | 9 |
| 16 | 24.580 | 3.6187 | 23 |
| 17 | 25.400 | 3.5037 | 4 |
| 18 | 26.520 | 3.3582 | 10 |
| 19 | 26.860 | 3.3165 | 14 |
| 20 | 27.800 | 3.2065 | 6 |
| 21 | 28.800 | 3.0974 | 20 |
| 22 | 29.980 | 2.9781 | 9 |
| 23 | 30.900 | 2.8915 | 15 |
| 24 | 31.140 | 2.8697 | 10 |
| 25 | 31.480 | 2.8395 | 7 |
| 26 | 32.100 | 2.7861 | 7 |
| 27 | 33.600 | 2.6650 | 3 |
| 28 | 37.940 | 2.3696 | 4 |
| 29 | 38.600 | 2.3306 | 5 |
| 30 | 39.620 | 2.2729 | 3 |
| 31 | 41.340 | 2.1822 | 10 |
| 32 | 43.320 | 2.0869 | 4 |
| 33 | 43.580 | 2.0751 | 9 |
| 34 | 46.380 | 1.9561 | 4 |
| 35 | 46.920 | 1.9349 | 15 |
| 36 | 49.780 | 1.8302 | 5 | it has characteristic absorption peaks at 3388.70, 3112.89, 1758.96, 1731.96, 1674.10, 1454.23, 1267.14, 950.84, 736.76 and 698.18cm$^{-1}$ in its infrared absorption spectrum, and it has an exothermic peak at 201° C. in its TG-DTA spectrum.

* * * * *